(12) United States Patent  
Burgi et al.

(10) Patent No.: US 8,657,833 B2
(45) Date of Patent: Feb. 25, 2014

(54) DOUBLE OFFSET SURGICAL TOOL HANDLE ASSEMBLY TO PROVIDE GREATER OFFSET FROM THE CORONAL PLANE

(75) Inventors: Jonas Burgi, Moutier (CH); Jeremy Degrave, Les Fontenelles (FR)

(73) Assignee: Greatbatch Medical S.A., Orvin (CH)

( * ) Notice: Subject to any disclaimer, the term of this patent is extended or adjusted under 35 U.S.C. 154(b) by 222 days.

(21) Appl. No.: 13/039,427

(22) Filed: Mar. 3, 2011

(65) Prior Publication Data

US 2012/0083769 A1  Apr. 5, 2012

Related U.S. Application Data

(60) Provisional application No. 61/310,903, filed on Mar. 5, 2010.

(51) Int. Cl.
*A61B 17/58* (2006.01)
*A61B 17/60* (2006.01)
*A61F 2/00* (2006.01)

(52) U.S. Cl.
USPC ................................................ 606/99

(58) Field of Classification Search
USPC ............. 606/79–85, 86 A, 86 B, 99, 280–299
See application file for complete search history.

(56) References Cited

U.S. PATENT DOCUMENTS

| D272,648 S | 2/1984 | Bolesky et al. |
| D273,806 S | 5/1984 | Bolesky et al. |
| 4,765,328 A | 8/1988 | Keller et al. |
| 4,921,493 A | 5/1990 | Webb, Jr. et al. |
| 5,089,003 A | 2/1992 | Fallin et al. |
| 5,124,106 A | 6/1992 | Morr et al. |
| 5,190,549 A * | 3/1993 | Miller et al. ............. 606/85 |
| 5,234,432 A | 8/1993 | Brown |
| 5,261,915 A | 11/1993 | Durlacher et al. |
| 5,324,293 A | 6/1994 | Rehmann |
| 5,342,362 A | 8/1994 | Kenyon et al. |
| 5,454,815 A | 10/1995 | Geisser et al. |
| 5,665,091 A | 9/1997 | Noble et al. |
| 5,707,374 A | 1/1998 | Schmidt |
| 5,993,455 A | 11/1999 | Noble |
| 6,120,508 A | 9/2000 | Grunig et al. |
| 6,663,636 B1 | 12/2003 | Lin |
| 7,591,821 B2 | 9/2009 | Kelman |
| 7,922,726 B2 | 4/2011 | White |
| 2005/0171548 A1 | 8/2005 | Kelman |
| 2007/0167952 A1* | 7/2007 | Burgi et al. ............. 606/99 |
| 2008/0004628 A1 | 1/2008 | White |
| 2008/0033444 A1 | 2/2008 | Bastian et al. |
| 2008/0255565 A1 | 10/2008 | Fletcher |

FOREIGN PATENT DOCUMENTS

WO    2006061708    6/2006

* cited by examiner

*Primary Examiner* — Andrew Yang
*Assistant Examiner* — Diana S Jones
(74) *Attorney, Agent, or Firm* — Michael F. Scalise

(57) ABSTRACT

A surgical tool handle for releasable connection to a surgical tool is described. The tool handle comprises a housing providing a linkage chamber extending from a proximal housing grip end to a distal housing tool end for receiving a tool. A tool linkage is partially housed within the linkage chamber. That way, manipulation of the tool linkage causes a locking pawl to pivot with respect to the housing from an open configuration ready to receive a tool for attachment to the housing to a closed configuration engageable with the tool supported at the distal housing tool end.

21 Claims, 7 Drawing Sheets

DOUBLE OFFSET SURGICAL TOOL HANDLE ASSEMBLY TO PROVIDE GREATER OFFSET FROM THE CORONAL PLANE

CROSS REFERENCE TO RELATED APPLICATION

This application claims priority to U.S. provisional application Ser. No. 61/310,903, filed on Mar. 5, 2010.

FIELD OF THE INVENTION

This invention relates to surgical tools for aiding in the installation of orthopedic prostheses in patients. More particularly, the present invention relates to an easily sterilizable handle assembly for use with a surgical tool in preparing a bone site, and for use in installing a prosthesis in the bone.

BACKGROUND OF THE INVENTION

Complicated surgical tool handles typically have crevices and recesses that are difficult to clean with relative ease without disassembly into separate component parts. Tool handles that are not properly cleaned and sterilized increase the risk of disease transfer from patient to patient. This is especially true following the emergence of certain "prions" that are not killed by normal hospital sterilization. A prion is a type of infectious agent made only of protein.

Further, in surgical procedures in which access to the treatment site is limited, it is difficult to use current solutions without subjecting the patient to repeated abrasion and tissue trauma when inserting and extracting surgical instruments.

Additionally, the insertion of a prosthetic implant is often problematic, and the orientation of the implant in a properly prepared recess is often critical to minimize recovery time of the patient. Still further, once the appropriate position of the tool is selected, it is often difficult to ensure that the position does not change upon insertion of the assembly through the incision.

It would be beneficial, therefore, to have an orthopedic tool handle that easily connects to a surgical tool, and that is readily adjustable, disassemblable, and cleanable. Additionally, it would be beneficial if the tool were partially disassembled for cleaning without the need to completely the component parts of the handle from each other. Further, it would be beneficial to have a handle that enables the surgeon to better maneuver and position a tool head to facilitate preparing a bone site to receive a prosthetic implant in a particular angular orientation.

SUMMARY OF THE INVENTION

A surgical tool handle aids a surgeon in controlling the use of a tool during surgery, for example, during preparation of a femoral cavity for reception of hip joint prosthesis. The present invention is such a surgical tool handle, but adapted to facilitate sterilization. That way, the present toll handle allows for partial disassembly to facilitate sterilization, while remaining loosely intact to prevent the separation of component parts from the device as a whole.

The present surgical handle assembly comprises a housing providing a linkage chamber housing a tool linkage. The housing extends from a proximal housing grip end to a distal housing tool end for receiving a tool. The tool linkage comprises: a handle lever attached to the housing by a proximal housing pivot pin to thereby provide a first pivotable connection between the tool linkage and the housing; a locking pawl attached to the housing by a distal housing pivot pin to thereby provide a second pivotable connection between the tool linkage and the housing; an inverted linkage comprising a proximal inverted linkage end and a distal inverted linkage end connected by a first free pivot pin to the handle lever to thereby provide a third pivotable connection; and a main linkage comprising a proximal main linkage end connected by a second free pivot pin to the proximal inverted linkage end adjacent to the proximal housing end in a fourth pivotable connection and a distal main linkage end connected by a third free pivot pin to the locking pawl adjacent to the distal housing end in a fifth pivotable connection.

During use, the handle lever is pivotable about the proximal housing pivot pin from a first, opened position spaced a maximum distance along a range of motion from the proximal housing end to a second, closed position spaced at a closer distance along the range of motion relative to the proximal housing end than the first position. This movement causes the inverted linkage, connected to the handle lever by the first free pivot pin, to move in a proximal direction to thereby move the main linkage, connected to the inverted linkage at the second free pivot pin, in a proximal direction toward the proximal housing end. This causes the locking pawl, connected to the distal main linkage end by the third free pivot pin, to pivot with respect to the housing on the distal housing pivot pin from an open configuration ready to receive a surgical tool for attachment to the housing to a closed configuration engageable with a surgical tool supported at the distal housing tool end.

In that respect, the present handle assembly is an adapted instrument used to prepare the cavity of the femur when the iliac crest is the main obstacle. For that reason, the handle assembly is adapted for an anterior approach where the offset from the coronal plane is large enough access to the femur even though the iliac crest prevents direct access to it.

These features of the present invention will be apparent upon consideration of the following detailed description in connection with the following drawings.

DETAILED DESCRIPTION OF THE PREFERRED EMBODIMENTS

Figure 1:
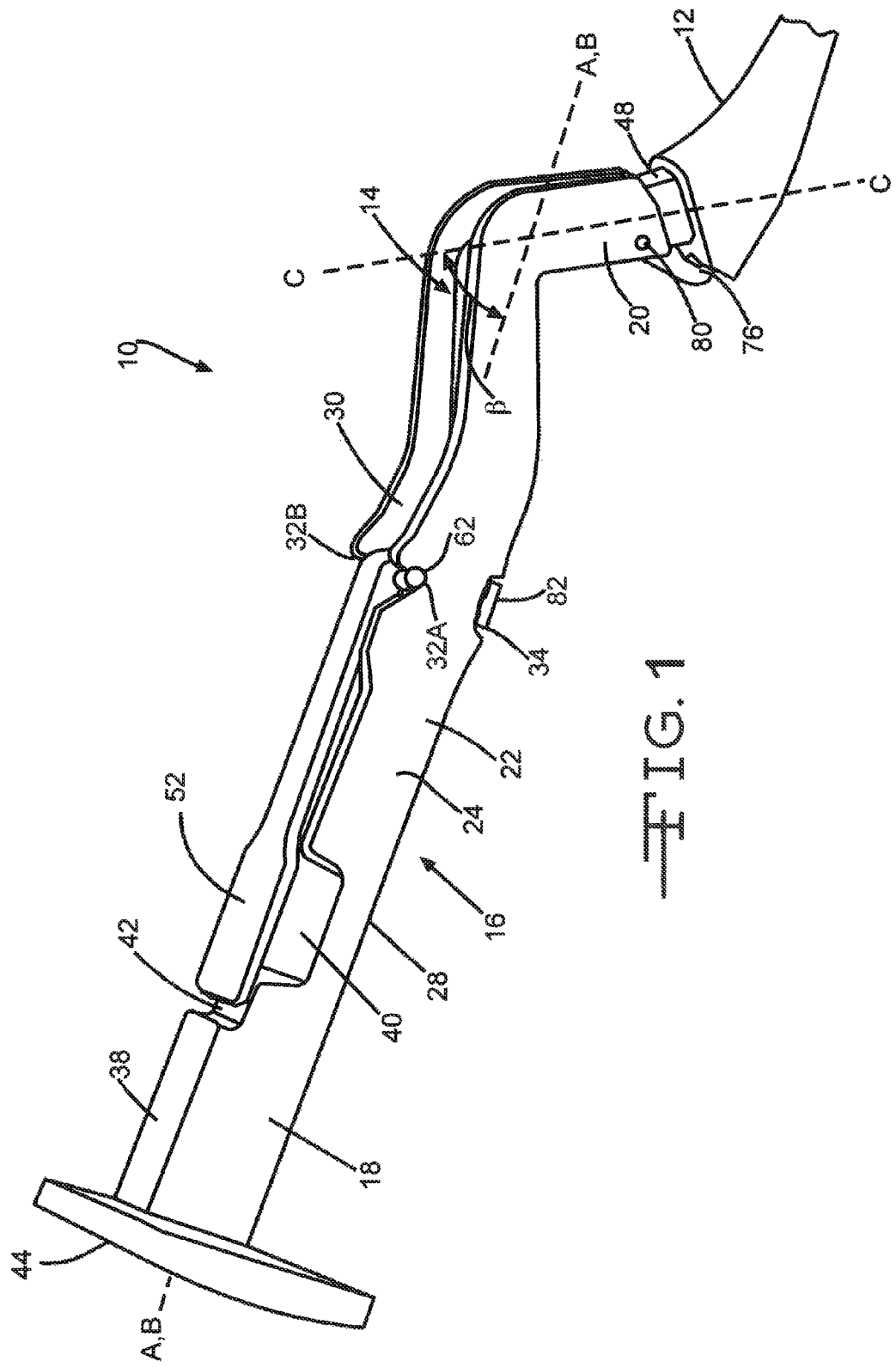
FIG. 1 is a perspective view of a rasp handle assembly 10 according to the present invention connected to a surgical tool 12.

Turning now to the drawings, FIGS. 1 to 4 and 7 illustrate a surgical handle assembly 10 according to the present invention. The handle assembly 10 is shown connected to a surgical tool, such as a broach or rasp 12 for performing a minimally invasive hip replacement surgery. Other tools useful with the handle assembly 10 include, but are not limited to, reamers, angled drivers, twist drills, flexible drills, cannulated drills, bayonet drills, bayonet taps, drill guides, adjustable angle drill guides, taps, and cannulated taps.

The handle assembly 10 generally comprises a linkage train 14 disposed within a housing 16. The housing 16 had a length that extends from a proximal housing section 18 to a distal neck section 20 with an intermediate housing section 22 there between. The intermediate housing section 22 comprises spaced apart right and left side walls 24 and 26 extending upwardly from a bottom wall 28 to an upper opening 30.

A unique feature of the present handle assembly 10 is that the intermediate housing section 22 is further comprised of an axial housing region 22A aligned along the axis A-A and an angled housing region 22B. As particularly shown in FIG. 3, the angled housing region 22B radiates in an outwardly direction with respect to the axis A-A, in either a leftward direction along an axis B-B or a rightward direction along axis B'-B' (shown in dashed lines). The angle α between axis B-B or B'-B' and axis A-A ranges from about 5° to about 35°, preferably about 15° to about 25°, and more preferably about 20°. This construction provides the intermediate section 22 having a linkage chamber with a generally U-shaped cross-section perpendicular to axes A-A and B-B (B'-B') extending from the proximal housing section 18. The bottom wall 28 is planar along the proximal housing section 18 and both the axial and angled regions 22A, 22B of the intermediate housing section 22.

A pair of aligned slots 32A, 32B, serving as catch recesses, extends from the upper opening 30 part-way into the height of the respective side walls 24, 26. A recess 34 is provided in the bottom wall 28 vertically below the aligned slots 32A, 32B. A pair of side-by-side vertical bores 36A, 36B (FIG. 3) extend from the recess 34 to the upper edges of the side walls 24, 26 proximally, but adjacent to the respective aligned slots 32A, 32B. The significance of the aligned slots 32A, 32B, the recess 34, and the vertical bores 36A, 36B will be discussed hereinafter.

The intermediate housing section 22 seamlessly meets the proximal housing section 18 having a generally rectangular shape in cross-section perpendicular to the axis A-A provided by the right and left side walls 24, 26, the bottom side wall 28 and an upper side wall 38. The upper side wall 38 is contoured to provide a finger grip region 40 adjacent to a ledge 42. A strike plate 44 is connected to the end of the proximal housing section 18.

The distal neck section 20 of the housing extends in a downwardly direction and angles back to align along a third axis C-C or C'-C' (FIG. 3) parallel to, but spaced from, the axis A-A. The angle β (FIG. 1) between both of the axes A-A and B-B (B'-B') and the axis C-C ranges from about 50° to about 80°, preferably about 60° to about 70°, and more preferably about 65°. The angular relationship of axis C-C is the same with both axes A-A and B-B because the latter, while angled with respect to each other, are aligned along a similar plane with respect to axis C-C.

In that manner, the right and left side walls 24, 26 forming the intermediate housing section 22 seamlessly extend distally and downwardly to form the distal neck section 20 of the housing. However, the bottom wall 28 ends spaced from the distal neck section 20. This provides a distal lower open slot 46 (FIG. 2) that is vertically below that portion of the upper opening 30 residing in the distal neck section 20. At the end of the distal neck section 20, the right and left side walls 22, meet a rectangularly-shaped portion with curved edges 48 supporting a nose 50.

As shown in FIGS. 1 to 4, the linkage train 14 resides inside the housing 16 and comprises a handle lever 52, an inverted linkage 54, a main linkage 56 and a locking pawl 58. The handle lever 52 includes a distal head 60 supporting a main fulcrum pin 62 having opposed ends extending outwardly from the handle lever head in an orientation aligned perpendicular to axis A-A. The opposed ends of pin 62 are received in the respective slots 32A, 32B while a proximal end 52A of the handle lever 52 rests on ledge 42. Moving in a proximal direction from the main fulcrum pin 62, the handle lever head 60 divides into spaced apart side walls 60A, 60B providing a gap there between.

Figure 6:
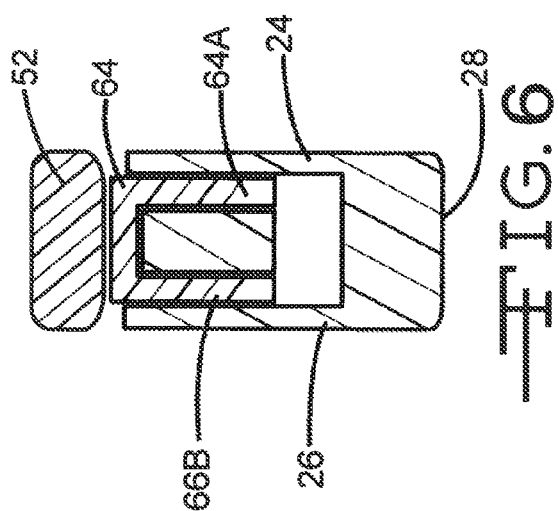
FIG. 6 is a cross-sectional view taken along line 6-6 of FIG. 2.
Figure 5:
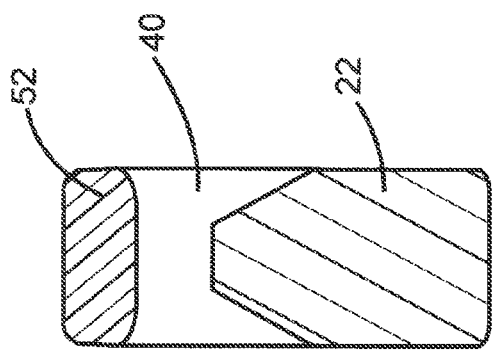
FIG. 5 is a cross-sectional view taken along line 5-5 of FIG. 2.
Figure 7:
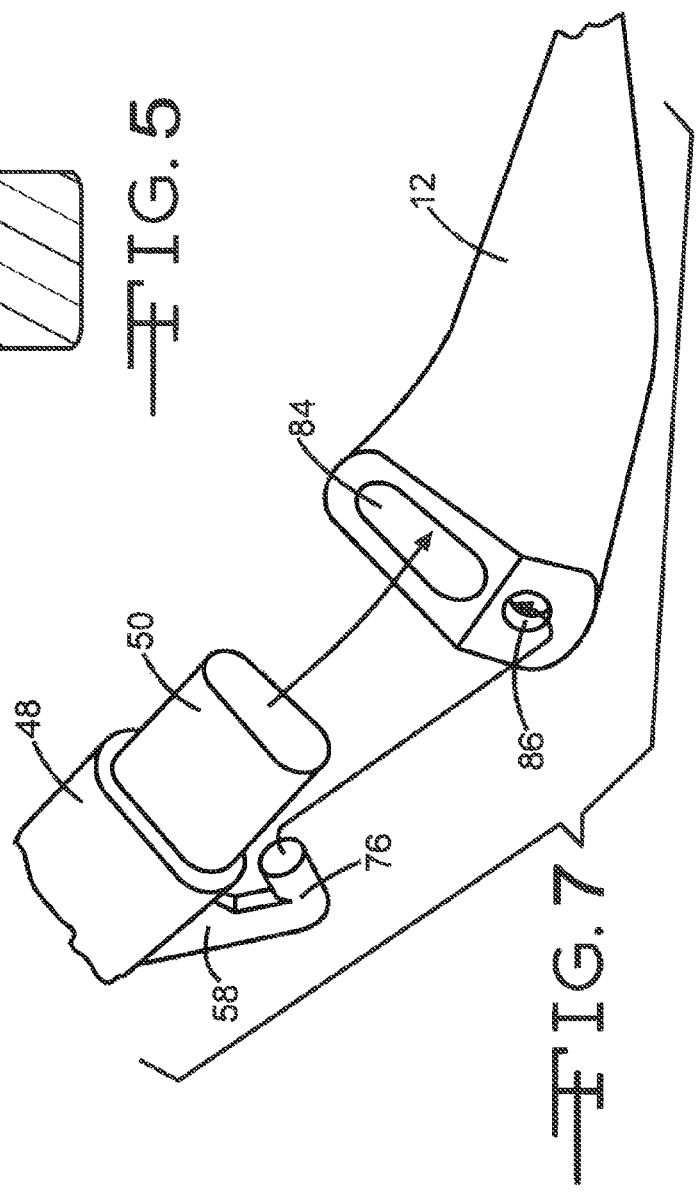
FIG. 7 is a broken-away view of the rasp handle assembly 10 shown in FIG. 1 prior to connection to the surgical tool 12.
Figure 8:
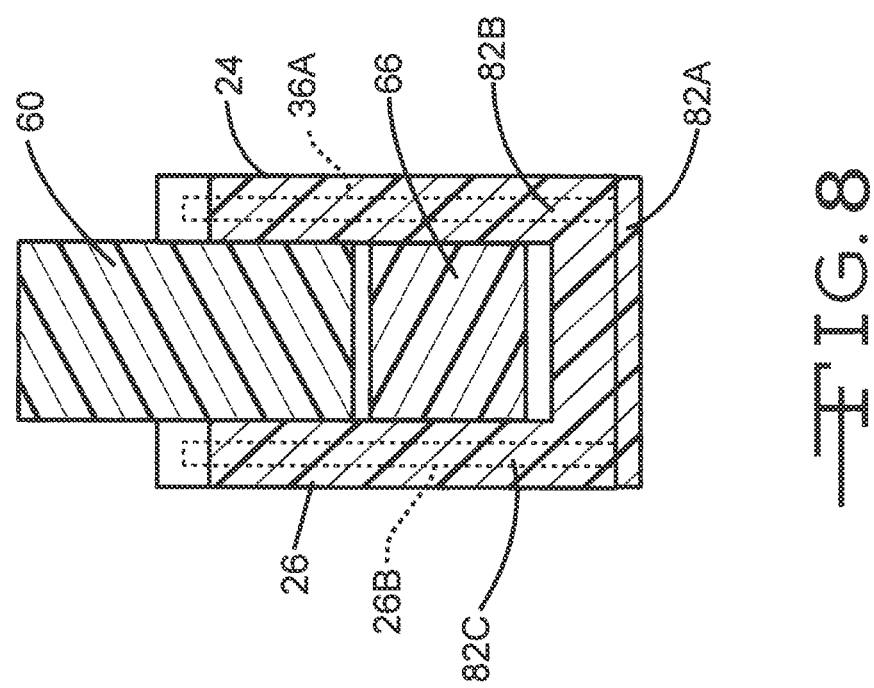
FIG. 8 is a cross-sectional view taken along line 8-8 of FIG. 2.

The inverted linkage 54 is a relatively short member extending from a downwardly angled proximal end 64 (FIG. 6) to a reduced cross-section distal end 66 (FIG. 8). The distal end 66 of the inverted linkage 54 is received in the gap provided between the opposed side walls 60A, 60B of the handle lever head 60. There, a pin 68 secures the inverted linkage 54 to the handle lever head 60 in a pivotable relationship.

The main linkage 56 is an elongate member having a proximal section 56A with its end received in a gap formed by spaced apart side walls 64A, 64B (FIG. 6) of the downwardly angled proximal end 64 of the inverted linkage 54 and being pivotably connected thereto by a pin 70. The proximal section 56A of the main linkage 56 is aligned with the axial region 22A of the intermediate housing section 22 along axis A-A. From there, and in a similar manner as the overall contour of the intermediate housing section 22, the main linkage 56 bends into an intermediate angled portion 56B that coincides with the angled region 22B of the intermediate housing section along axis B-B until it forms into a distal fork portion 56C. The distal fork portion 56C extends in a downwardly direction at an angle similar to that of the angled housing portion 20 along axis C-C.

A pair of opposed lateral protrusions 72 extend outwardly from the proximal section 56A of the main linkage 56 adjacent to its pivotable connection with the downwardly angled proximal end 64 of the inverted linkage 54. When the linkage train 14 resides inside the housing 16, these protrusions 72 are in a closely spaced, but movable relationship with the inner surfaces of the right and left housing side walls 24, 26. That way, they help stabilize the linkage train 14 inside the housing 16 as the linkage train is manipulated to lock onto and release from a rasp tool 12, as will be described in detail hereinafter.

The locking pawl 58 is another relatively short member extending from a reduced cross-section proximal end 74 to an upwardly extending hook 76. The proximal end 74 of the locking pawl 58 is received in the distal fork portion 56C of the main linkage 56. A pin 78 secures the main linkage 56 to the locking pawl 58 in a pivotable relationship. Further, a housing pivot pin 80 extends through the locking pawl 58 at an intermediate location between the proximal end 74 and the upwardly extending hook 76. The opposed ends of the pivot pin 80 are received in openings in the right and left housing side walls 24, 26 flush with the respective outer surfaces thereof. That way, the hook 76 of the locking pawl 58 is pivotable about a range of motion vertically below the reinforcing nose 50 of the housing 16.

With the linkage train 14 residing inside the right and left side walls 24, 26 and the bottom wall 28 comprising the housing 16, the main linkage 56 extends from the axial housing region 22A of the intermediate housing section 22 at a position adjacent to the proximal housing section 18, along the angled housing region section 22B and to the distal housing neck section 20. The distal neck section 20 is where the main linkage 56 pivotably connects to the locking pawl 58. The opposite, proximal section 56A of the main linkage 56 pivotably connects to the inverted linkage 54 in the intermediate housing section 22 adjacent to the proximal housing section 18 and at a location proximal of the aligned slots 32A, 32B in the respective housing side walls 24, 26.

The inverted linkage 54 is disposed vertically above the main linkage 56. The downwardly angled proximal end 64 of the inverted linkage 54 accommodates this vertically aligned relationship. As previously discussed, the opposed distal end 66 of the inverted linkage 54 is pivotably connected to the handle lever 52 at the pivot pin 68, which is proximal of the main fulcrum pin 62 pivotably received in the respective slots 32A, 32B of the right and left side walls 24, 26 of the housing 16.

As particularly shown in FIG. 8, a linkage lock mechanism 82 comprises a base plate 82A having a pair of opposed upwardly extending blocking pins 82B, 82C supported thereon. As further illustrated in FIGS. 1 to 4, when the linkage train 14 resides in the housing 16 with the main fulcrum pin 62 seated in the slots 32A, 32B, the linkage lock mechanism 82 is moved into position with the blocking pins 82B, 82C residing in the bores 36A, 36B in the respective side walls 24, 26. With the base plate 82A seated in the housing recess 34, the distal ends of the pins 82B, 82C extend upwardly beyond the upper edges of the side walls 24, 26. These extending portions of pins 82B, 82C block the fulcrum pin 62 and, consequently, the linkage train 14 from being removed from inside the housing 16. It should be noted that the pivotable connection between the locking pawl 58 and the distal neck section 20 of the housing 16 at pin 80 prevents the linkage train 14 from being completely separate from the housing.

Because they are supported on side walls comprising the housing, the fulcrum pin 62 and the pivot pin 80 are referred to in the claims as "housing pivot pins". That is regardless whether they are intended to be removable from their supported relationship with the housing, as in the case of fulcrum pin 62, or not, as in the case of pivot pin 80. The other pivot pins 68, 70 and 78 are referred to as "free pivot pins". That is because those latter pivot pins provide for pivotable movement between the various linkage members they connect together without being supported on the housing.

In use, the handle assembly 10 is detachably connectable to a surgical tool 12, such a broach or rasp, by lifting the handle lever 52 in an upwardly direction, away from the housing ledge 42. Manipulation is aided by the finger recess 40. As the proximal end of the handle lever 52 move upwardly, its distal head 60 pivots on the fulcrum pin 62 received in the aligned slots 32A, 32B. This movement causes the pivot pin 68 to move upwardly and distally to a position essentially vertically aligned directly above the fulcrum pin 62. In turn, the inverted linkage 54 moves in an upwardly and distal direction, toward the housing neck section 20. As the inverted linkage 54 moves, the main linkage 56, pivotably connected thereto at pin 70, follows along. This causes the distal fork portion 56C of the main linkage 56 to move both forwardly or proximally and upwardly between the housing side walls 24, 26. In turn, the locking pawl 58 pivots on the housing pivot pin 80 to move its hook portion 76 from a closely spaced relationship with the housing reinforcing extension 50 to a second position, spaced further away than the first position.

Figure 4:
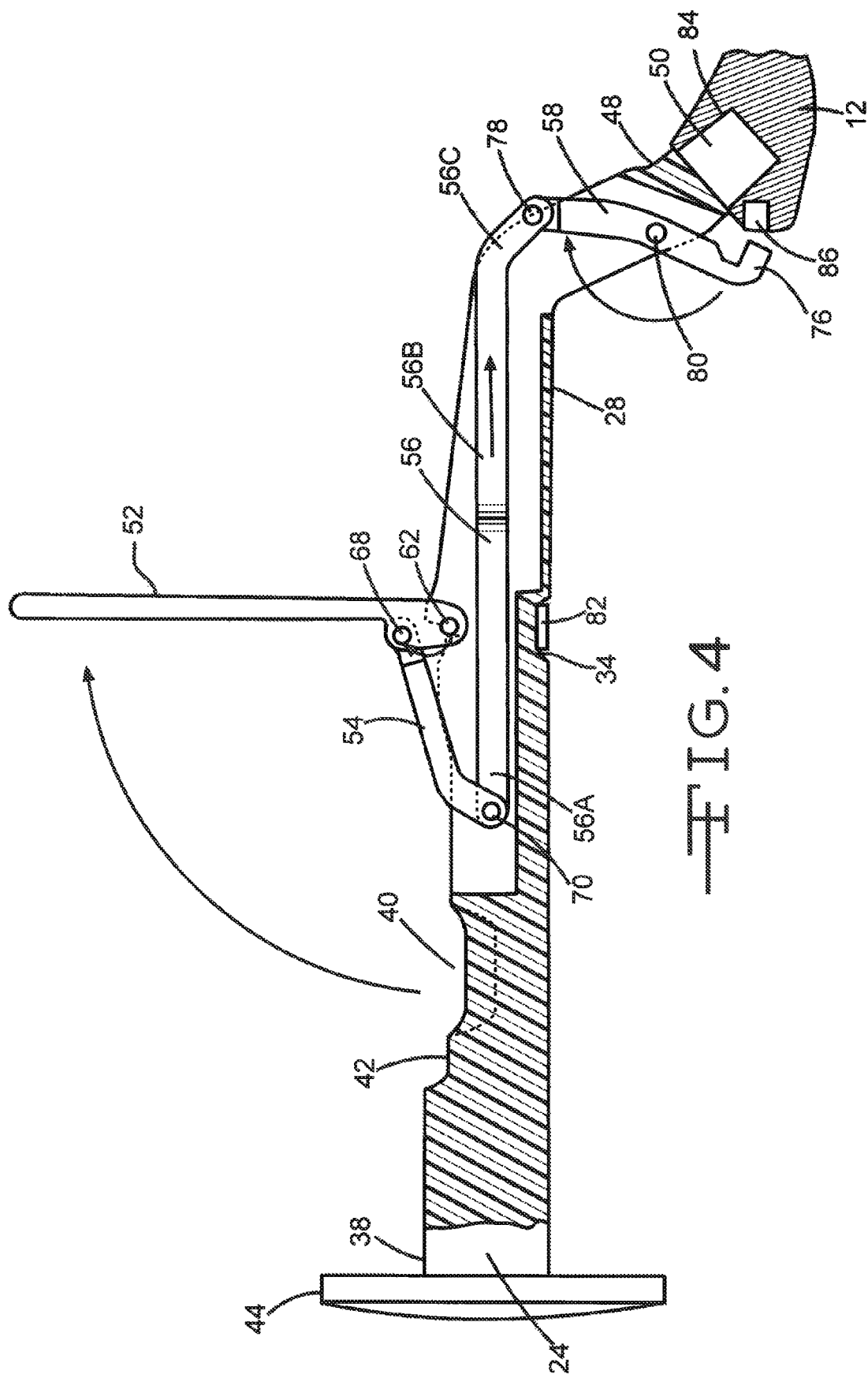
FIG. 4 is a side, cross-sectional view of the rasp handle assembly 10 shown in FIG. 1 prior to connection to the surgical tool 12.

As shown in FIG. 4, a surgical rasp 12, or similar tool comprising a body designed to wear or cut bone and cartilage by friction, is now mountable onto the handle assembly 10. The surgical tool 12 is provided with a main inlet 84 and a secondary inlet 86. The main inlet 84 is sized and configured to receive the housing reinforcing extension 50 in a snug, but slidable fit. The secondary inlet 86 is now aligned with the hook portion 76. A locked relationship between the handle assembly 10 and the surgical tool 12 is affected when the handle lever 42 is returned to its original position, resting against the ledge 42. That return movement causes the locking pawl 58 to pivot on the housing pivot pin 80 to move the hook portion 76 back to the closely spaced relationship with the housing reinforcing extension 50, to thereby reside in the secondary rasp inlet 86. As the locking pawl 58 pivots back to its original position, the main linkage 56 moves proximally, which cause the inverted linkage 54 to move in a downwardly and proximal direction as it returns to its original position vertically above the main linkage 56.

Figure 2:
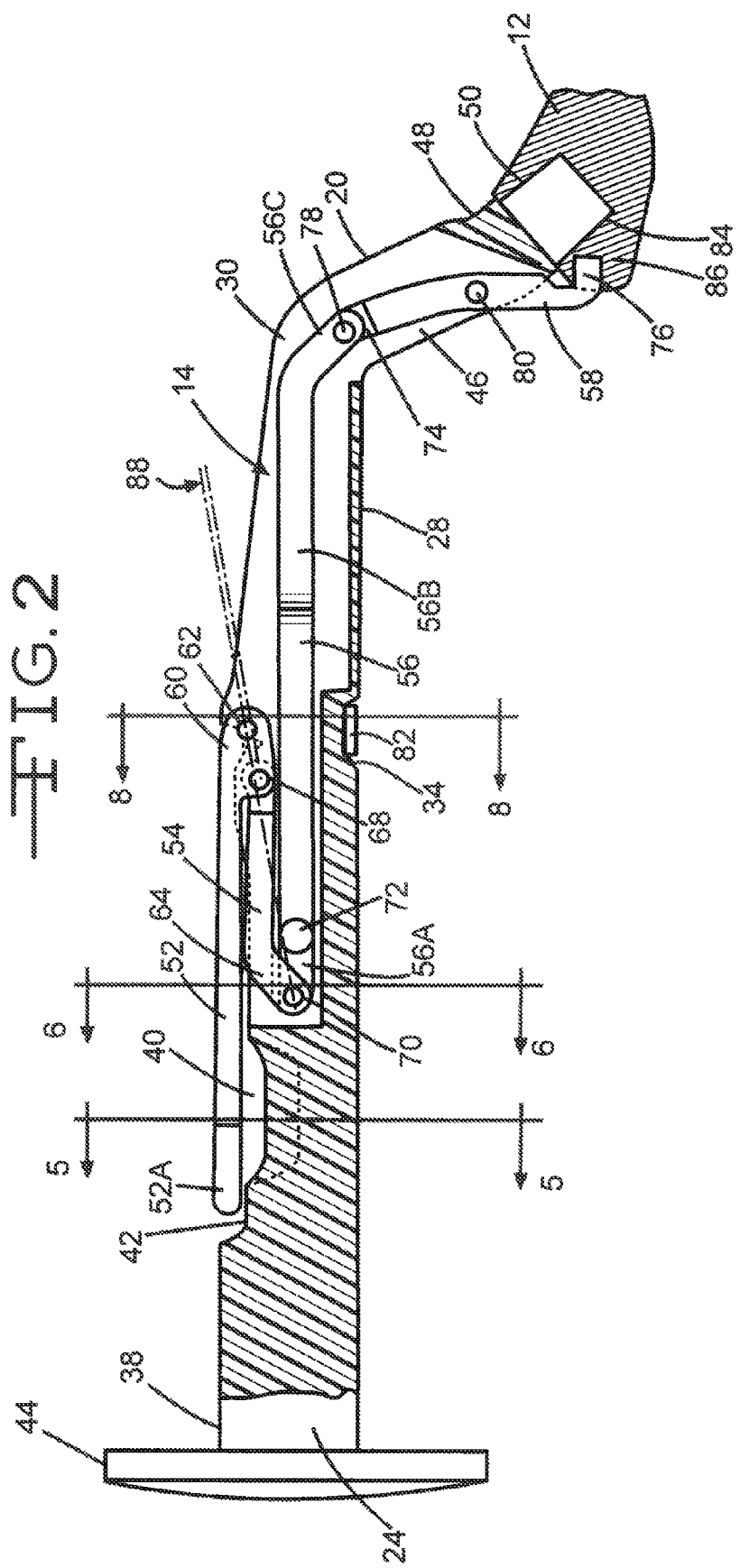
FIG. 2 is a side, cross-sectional view of the rasp handle assembly 10 shown in FIG. 1 connected to a surgical tool 12.
Figure 3:
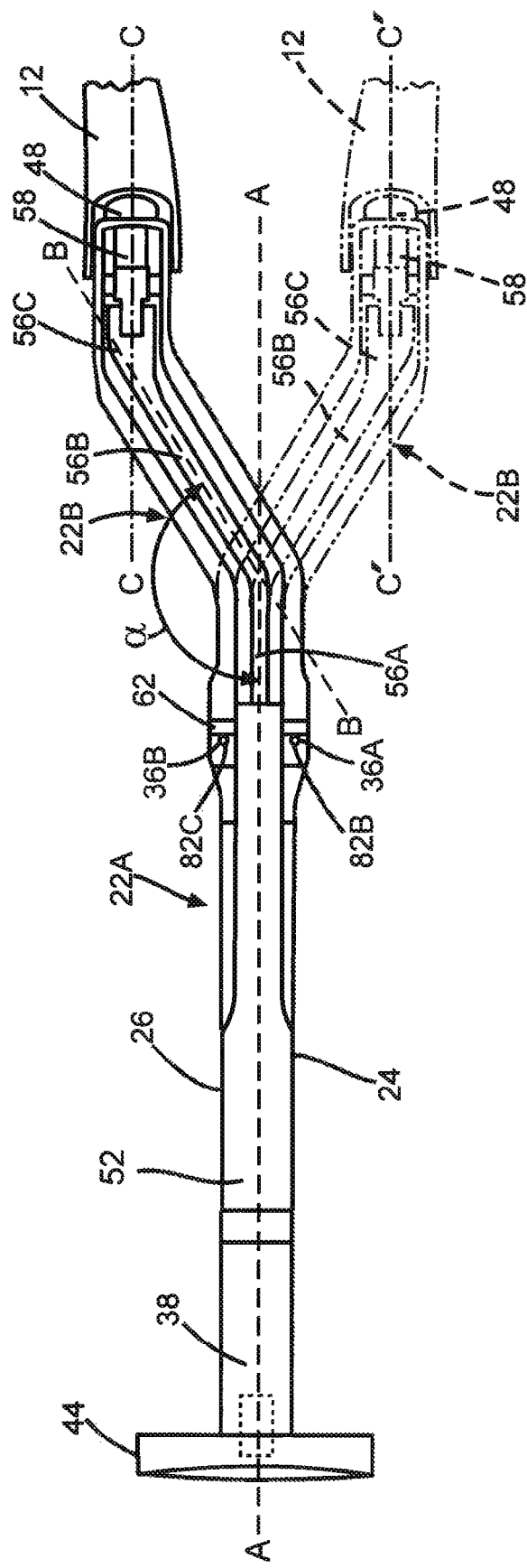
FIG. 3 is a plan view of the rasp handle assembly 10 of FIG. 1 connected to the surgical tool 12 and showing alternate right and left angled embodiments.

As shown in FIG. 2, the drive train 14 is locked into position once the first pivot pin 68 is vertically below the fulcrum pivot pin 62 in an "over center" relationship. The over center, locked condition is indicated by arrow 88 as the gap between the two dashed lined centered on pins 62 and 68 with respect to the center of the second pivot pin 70. The surgical tool 12 is now firmly locked and secured to the handle assembly 10 for use during a surgical procedure.

Figure 9:
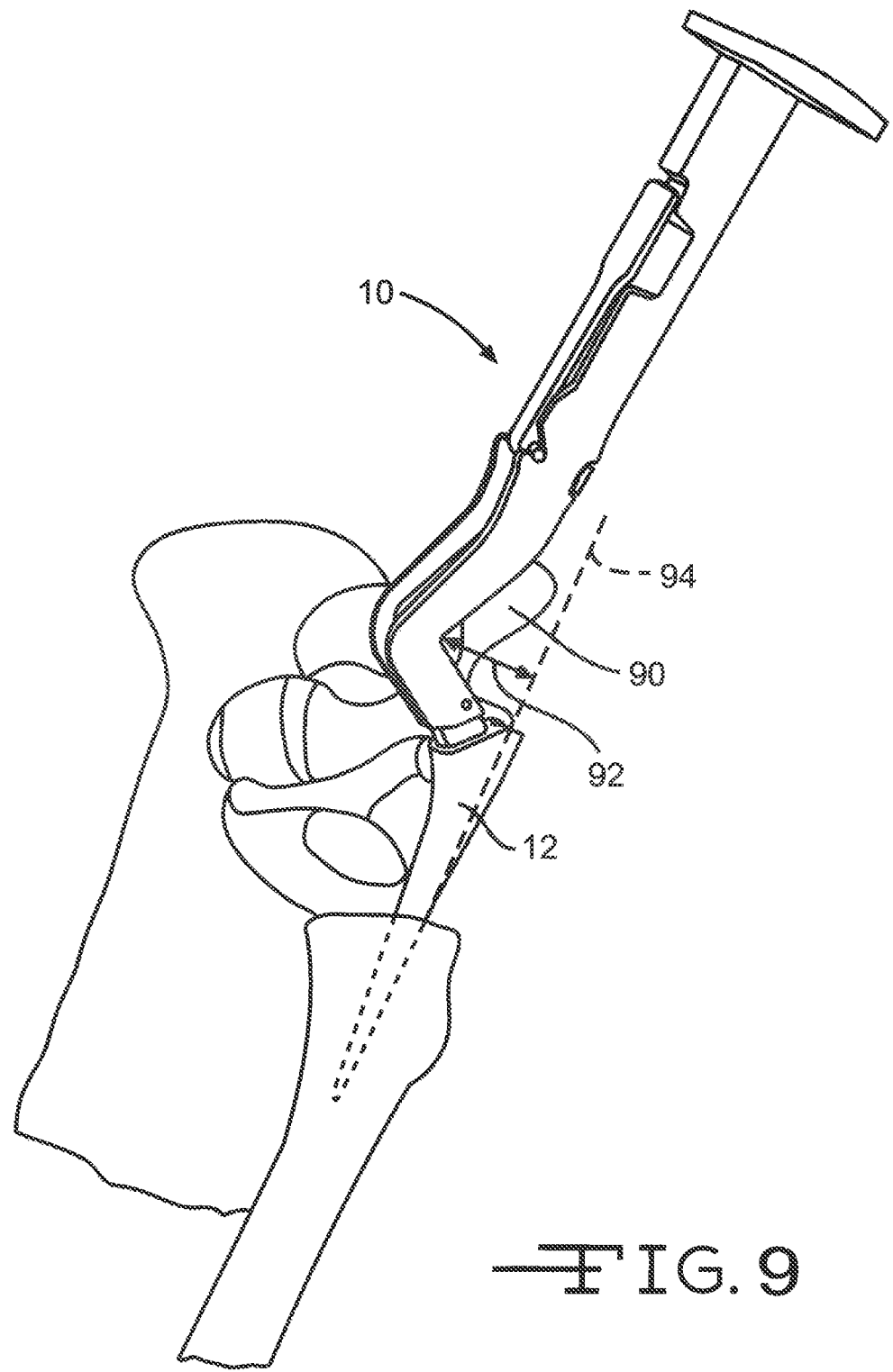
FIG. 9 is an illustration of the present handle assembly 10 connected to a rasp 12 during use in a minimally invasive hip surgery procedure where the iliac crest is blocking direct access to the femur.

The angular relationship between the various axes A-A, B-B (B'-B') and C-C provide the present tool handle assembly 10 as being particularly useful for performing minimally invasive hip surgery. For minimally invasive surgery of the hips, most surgeons perform an anterolateral approach known as the Roettinger technique (or Watson-Jones). Depending on the country, some variant of this technique is commonly used. As shown in FIG. 9, the handle assembly 10, however, is an adapted instrument that is used to prepare the cavity of the femur when the iliac crest 90 is the main obstacle. In that respect, the present handle assembly 10 is adapted for an anterior approach where the offset 92 from the coronal plane 94 must be increased to approximately 50 mm. The drawing illustrates use of the handle assembly 10 in a minimally invasive hip surgery procedure where the iliac crest is blocking direct access to the femur.

To prepare the handle assembly 10 for cleaning and sterilization, the linkage lock mechanism 82 is manipulated in a direction away from the housing 16 until the blocking pins 82A, 82B are completely removed from the bores 36A, 36B in the respective side walls 24, 26. The linkage train 14 including the handle lever 52, inverted linkage 54 and main linkage 56 is now pivotable out of the housing 16 about housing pivot pin 80. The pivot pin 80 keeps the linkage train 14 from being completely separated from the housing 16. Thus, the linkage train 14 is separable from the housing 16 in a manner that is sufficient to clean and sterilize all of their parts without the possibility of there being total separation of one for the other. Total separation could easily lead to lost and misplaced parts.

The present invention further relates to the handle assembly 10 comprising part of a kit. Typically, a surgical kit comprises a container, the handle assembly 10, and a surgical tool 12 to be connected to the handle assembly. Representative surgical tools 12 include, but are not limited to, broaches, rasps, reamers, angled drivers, twist drills, flexible drills, cannulated drills, bayonet drills, bayonet taps, drill guides, adjustable angle drill guides, taps, and cannulated taps.

Instructions for connecting the surgical tool to the handle assembly 10 are also typically provided with the kit.

Additionally, the linkage train 14 and housing 16 are preferably made of a durable material that can be washed and sterilized (e.g., with high heat) to comply with sterilization standards known in the art. In one embodiment, the linkage train 14 and housing 16 are made of metal, such as stainless or a super alloy material. In another embodiment, they are made of a composite material. Though the illustrated embodiment shows the housing 16 as being one piece, in other embodiments it can be modular to facilitate disassembly of the handle assembly 10.

Of course, the foregoing description is that of certain features, aspects and advantages of the present invention, to which various changes and modifications can be made without departing from the spirit and scope of the present invention. Moreover, the handle assembly need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention.

What is claimed is:

1. A surgical tool handle, which comprises:
   a) a housing providing a linkage chamber extending from a proximal housing section providing a grip end to an intermediate angled housing region connected to a distal housing neck section providing a tool end for receiving a tool, wherein the proximal housing section is aligned along a longitudinal A-A and the angled housing region extends along an axis B-B;
   b) a tool linkage at least partially housed within the linkage chamber, the tool linkage comprising:
      i) a handle lever attached to the housing by a proximal housing pivot pin to thereby provide a first pivotable connection between the tool linkage and the housing;
      ii) a locking pawl attached to the housing by a distal housing pivot pin to thereby provide a second pivotable connection between the tool linkage and the housing;
      iii) an inverted linkage comprising a proximal inverted linkage end and a distal inverted linkage end connected by a first free pivot pin to the handle lever to thereby provide a third pivotable connection; and
      iv) a main linkage comprising a proximal main linkage end connected by a second free pivot pin to the proximal inverted linkage end adjacent to the proximal housing section in a fourth pivotable connection and a distal main linkage end connected by a third free pivot pin to the locking pawl adjacent to the distal housing section in a fifth pivotable connection,
      v) wherein the locking pawl is disposed within the distal housing neck section having a longitudinal axis C-C that is parallel to, but spaced from, the axis A-A; and
   c) wherein the handle lever is pivotable about the proximal housing pivot pin from a first, opened position spaced a maximum distance along a range of motion from the proximal housing section to a second, closed position spaced at a closer distance along the range of motion relative to the proximal housing section than the first position to thereby cause the inverted linkage, connected to the handle lever by the first free pivot pin, to move in a proximal direction to thereby move the main linkage, connected to the inverted linkage at the second free pivot pin, in a proximal direction toward the proximal housing section, to thereby cause the locking pawl, connected to the distal main linkage end by the third free pivot pin, to pivot with respect to the housing on the distal housing pivot pin from an open configuration ready to receive a tool for attachment to the housing to a closed configuration detachably secured to a tool supported at the distal housing tool end.

2. The surgical tool handle of claim 1 wherein the proximal housing pivot pin is supported on the housing in a pair of catch recesses at a position that is distal with respect to the grip end of the proximal housing section, to thereby pivotably mount the handle lever to the housing.

3. The surgical tool handle of claim 2 wherein the proximal housing pivot pin is selectively removable from the pair of catch recesses provided in the housing.

4. The surgical tool handle of claim 1 wherein the distal housing pivot pin is not separable from the housing.

5. The surgical tool handle of claim 1 wherein with the handle lever in the second, closed position, the third pivotable connection between the distal inverted linkage end and the handle lever at the first free pivot pin is more proximal than the first pivotable connection of the handle lever and the housing at the proximal housing pivot pin.

6. The surgical tool handle of claim 1 wherein the distal housing pivot pin pivotally supports the tool linkage for pivotable movement out of the linkage chamber for cleaning with the tool linkage remaining connected to the housing at the second pivotable connection of the distal housing pivot pin.

7. The surgical tool handle of claim 1 wherein the tool linkage is removably attached to the housing at the proximal housing pivot pin by a linkage lock mechanism such that when the linkage lock mechanism is in a release position, the tool linkage is pivotable out of the linkage chamber for cleaning with the tool linkage remaining connected to the housing at the second pivotable connection of the distal housing pivot pin.

8. The surgical tool handle of claim 1 wherein linkage lock mechanism comprises a base plate supporting a pair of side-by-side pins that are received in the housing to block release of the fulcrum pin from removal out of a pair of catch recesses on the housing.

9. The surgical tool handle of claim 1 wherein the angled housing region extends longitudinally along the axis B-B from the proximal housing section to the distal housing section.

10. The surgical tool handle of claim 9 wherein axes A-A and B-B are offset from each other in a range of from about 5° to about 35°.

11. The surgical tool handle of claim 9 wherein axes A-A and B-B are offset from each other at about 20°.

12. The surgical tool handle of claim 9 wherein the axis B-B angles either in a rightward or a leftward direction with respect to the axis A-A.

13. The surgical tool handle of claim 9 wherein the housing comprises a bottom wall that is planar along both the proximal housing section and the angled housing region aligned along axes A-A and B-B.

14. The surgical tool handle of claim 13 wherein the distal housing neck section angles in a downwardly direction of from about 50° to about 80° with respect to the planar bottom of the proximal housing section and the angled housing region.

15. The surgical tool handle of claim 13 wherein the distal housing neck section angles in a downwardly direction of about 65° with respect to the planar bottom of the proximal housing section and the angled housing region.

16. The surgical tool handle of claim 1 wherein a strike plate is attached to the grip end of the proximal housing section.

17. The surgical tool handle of claim 1 wherein a reinforcing extension is provided at the distal housing tool end to reinforce a connection between the handle and a surgical tool.

18. The surgical tool handle of claim 1 wherein the inverted linkage is disposed vertically above the main linkage.

19. A kit, comprising:
  a) a container;
  b) a surgical tool handle according to claim 1, wherein the surgical tool handle is disposed within the container; and
  c) a tool to be connected to the surgical tool handle, wherein the tool is selected from a group consisting of broaches, rasps, reamers, angled drivers, twist drills, flexible drills, cannulated drills, bayonet drills, bayonet taps, drill guides, adjustable angle drill guides, taps, and cannulated taps.

20. The kit of claim 19 comprising instructions for connecting the tool to the surgical tool handle.

21. A surgical tool handle, which comprises:
  a) a housing providing a linkage chamber extending from a proximal housing section providing a grip end to an intermediate angled housing region connected to a distal housing neck section providing a tool end for receiving a tool, wherein the proximal housing section is aligned along a longitudinal A-A and the angled housing region extends longitudinally along an axis B-B from the proximal housing section to the distal housing neck section, and wherein the housing comprises a bottom wall that is planar along both the proximal housing section and the angled housing region aligned along axes A-A and B-B;
  b) a tool linkage at least partially housed within the linkage chamber, the tool linkage comprising:
    i) a handle lever attached to the housing by a proximal housing pivot pin to thereby provide a first pivotable connection between the tool linkage and the housing;
    ii) a locking pawl attached to the housing by a distal housing pivot, pin to thereby provide a second pivotable connection between the tool linkage and the housing;
    iii) an inverted linkage comprising a proximal inverted linkage end and a distal inverted linkage end connected by a first free pivot pin to the handle lever to thereby provide a third pivotable connection; and
    iv) a main linkage comprising a proximal main linkage end connected by a second free pivot pin to the proximal inverted linkage end adjacent to the proximal housing section in a fourth pivotable connection and a distal main linkage end connected by a third free pivot pin to the locking pawl adjacent to the distal housing neck section in a fifth pivotable connection,
    v) wherein the locking pawl is disposed within the distal housing neck section, the distal housing neck section being disposed along a longitudinal axis C-C that is parallel to, but spaced from, the axis A-A and wherein the distal housing neck section angles in a downwardly direction of from about 50° to about 80° with respect to the planar bottom of the proximal housing section and the angled housing region; and
  c) wherein the handle lever is pivotable about the proximal housing pivot pin from a first, opened position spaced a maximum distance along a range of motion from the proximal housing section to a second, closed position spaced at a closer distance along the range of motion relative to the proximal housing section than the first position to thereby cause the inverted linkage, connected to the handle lever by the first free pivot pin, to move in a proximal direction to thereby move the main linkage, connected to the inverted linkage at the second free pivot pin, in a proximal direction toward the proximal housing section, to thereby cause the locking pawl, connected to the distal main linkage end by the third free pivot pin, to pivot with respect to the housing on the distal housing pivot pin from an open configuration ready to receive a tool for attachment to the housing to a closed configuration detachably secured to a tool supported at the distal housing tool end.

* * * * *